United States Patent [19]
Bhalani et al.

[11] Patent Number: 5,858,401
[45] Date of Patent: Jan. 12, 1999

[54] PHARMACEUTICAL COMPOSITION FOR CYCLOSPORINES

[75] Inventors: Vinayak T. Bhalani; Satishchandra P. Patel, both of Livingston, N.J.

[73] Assignee: Sidmak Laboratories, Inc., East Hanover, N.J.

[21] Appl. No.: 786,314

[22] Filed: Jan. 22, 1997

Related U.S. Application Data

[60] Provisional application No. 60/010,410 Jan. 22, 1996.
[51] Int. Cl.$^6$ ..................................................... A61K 9/48
[52] U.S. Cl. ............................ 424/450; 424/405; 514/723
[58] Field of Search .................................. 424/455, 489, 424/456, 461, 450; 514/773, 11

[56] References Cited

U.S. PATENT DOCUMENTS

| | | |
|---|---|---|
| 2,870,062 | 1/1959 | Stanley et al. . |
| 4,388,307 | 6/1983 | Cavanak . |
| 4,428,927 | 1/1984 | Ebert et al. . |
| 4,649,047 | 3/1987 | Kaswan . |
| 4,711,902 | 12/1987 | Serno . |
| 4,719,239 | 1/1988 | Muller et al. . |
| 4,722,941 | 2/1988 | Echert et al. . |
| 4,722,999 | 2/1988 | Handschumacher et al. . |
| 4,727,109 | 2/1988 | Schmidt et al. . |
| 4,792,449 | 12/1988 | Ausman et al. . |
| 4,795,643 | 1/1989 | Seth . |
| 4,839,342 | 6/1989 | Kaswan . |
| 4,888,239 | 12/1989 | Brox . |
| 4,914,188 | 4/1990 | Dumont et al. . |
| 4,935,243 | 6/1990 | Borkan et al. . |
| 4,963,362 | 10/1990 | Rahman et al. . |
| 4,990,337 | 2/1991 | Kurihara et al. . |
| 4,996,193 | 2/1991 | Hewitt et al. ............................ 514/11 |
| 5,047,396 | 9/1991 | Orban et al. . |
| 5,047,512 | 9/1991 | Handschumacher et al. . |
| 5,051,402 | 9/1991 | Kurihara et al. . |
| 5,118,493 | 6/1992 | Kelley et al. . |
| 5,120,710 | 6/1992 | Liedtke . |
| 5,154,930 | 10/1992 | Popescu et al. ........................ 424/489 |
| 5,206,219 | 4/1993 | Desai . |
| 5,294,604 | 3/1994 | Nussenblatt et al. . |
| 5,342,625 | 8/1994 | Hauer et al. . |
| 5,376,381 | 12/1994 | Weiner et al. . |
| 5,411,952 | 5/1995 | Kaswan . |
| 5,431,916 | 7/1995 | White . |
| 5,444,041 | 8/1995 | Owen et al. . |
| 5,474,979 | 12/1995 | Ding et al. . |
| 5,478,860 | 12/1995 | Wheeler et al. . |
| 5,504,068 | 4/1996 | Komiya et al. . |
| 5,583,105 | 12/1996 | Kovacs et al. . |
| 5,589,455 | 12/1996 | Woo . |
| 5,603,951 | 2/1997 | Woo . |
| 5,614,491 | 3/1997 | Walch et al. . |
| 5,635,497 | 6/1997 | Molenaar . |
| 5,639,474 | 6/1997 | Woo . |
| 5,639,724 | 6/1997 | Cavanak . |
| 5,645,856 | 7/1997 | Lacy et al. .............................. 424/455 |
| 5,652,212 | 7/1997 | Cavanak et al. . |
| 5,660,858 | 8/1997 | Parikh et al. . |
| 5,716,928 | 2/1998 | Benet et al. . |

FOREIGN PATENT DOCUMENTS

| | | |
|---|---|---|
| 2015339 | 9/1979 | United Kingdom . |
| 2222770 | 3/1990 | United Kingdom . |
| 2228198 | 8/1990 | United Kingdom . |
| 2257359 | 1/1993 | United Kingdom . |
| 9210996 | 7/1992 | WIPO . |
| 9221348 | 12/1992 | WIPO . |

OTHER PUBLICATIONS

Copy of Computer Searches.
Certifcate o Analysis on CAPMUL MCM C8, dated Feb. 6, 1997, from Abitec Corp.
Test Results on dl–x–tocopherol USP, dated Jul. 7, 1997, from Hoffman–LaRoche Inc.
Certificate of Analysis for CAPTEX 300, dated Jun. 25, 1996, from Abitec Corp.
Product Information for CAPTEX 300, undated, from Abitec Corp.
Certificate of Analysis for CAPMUL MCM, dated Mar. 17, 1997, from Abitec Corp.
Product Information for CAPMUL MCM, dated Mar. 1994, form Abitec Corp.
Manufacturer's Test Certificate for IMWITOR 308, dated Sept 1, 1995, from Hüls AG.
Certificate of Analysis on polysorbate 80, dated Jun. 24, 1996, from Spectrum Quality Products, Inc.
Data Sheet for LABRASOL, dated 1992, form Gattefossé Corp. (2 pages).
Technical Bulletin for CREMOPHOR EL, dated Apr. 1996, from BASF Corp.
Data Sheet for LABRAFAC LIPOPHILE WL 1349, dated 1992 (2 pages).
Product Information on CAPMUL MCM C8, dated Oct. 31, 1996, from Abitec Corp.

*Primary Examiner*—Thurman K. Page
*Assistant Examiner*—William E. Benston, Jr.
*Attorney, Agent, or Firm*—Greenblum & Bernstein, P.L.C.

[57] ABSTRACT

The invention comprises a stable solution of cyclosporine forming a polar lipid self-emulsifying drug delivery system ("PLSEDDS"). The composition typically consists of cyclosporine dissolved in a polar lipid, such as a medium chain monoglyceride of $C_6$–$C_{12}$ fatty acids having a monoglyceride content of at least 50% and a surfactant. The composition provided here instantly forms a fine emulsion on exposure to water. The encapsulated dosage form of this composition needs neither a hydrophilic component nor air-tight blister packaging, and is particularly suitable for oral administration.

24 Claims, No Drawings

PHARMACEUTICAL COMPOSITION FOR CYCLOSPORINES

CROSS REFERENCE TO RELATED APPLICATIONS

This application claims the benefit of U.S. Provisional application Ser. No. 60/010,410, filed Jan. 22, 1996, the disclosure of which is incorporated by reference in its entirety.

BACKGROUND

Cyclosporines form a class of polypeptides commonly possessing immunosuppressive and anti-inflammatory activity. The most commonly known cyclosporine is cyclosporine-A. It is commercially available as Sandimmune® in a soft gelatin capsule dosage form. Other forms of cyclosporines include cyclosporine-B, -C, -D, and their derivatives. It should be understood that in this specification the terms "cyclosporine" or "cyclosporines" refer to any of the several cyclosporines or to any mixture of the several cyclosporines.

Cyclosporine is a hydrophobic material exhibiting poor bioavailability. The liquid oral formulations containing oils, ethanol and a trans-esterification product of a triglyceride and a polyol as a surfactant (U.S. Pat. No. 4,388,307) have a variety of difficulties, such as unpleasant taste, which is unacceptable for long-term therapy. The use of the soft gelatin capsule dosage to mask the taste of the solution entails specialized packaging of the encapsulated product in an air tight blister or aluminum foil blister package. This renders the product more bulky and more expensive. The storage conditions are far from ideal.

The bioavailability of these liquid formulations or the soft gelatin capsule formulation containing ethanol, oils and Labrafil surfactant, is low and variable, and reported to be about 30%.

Recently, U.S. Pat. No. 5,342,625 was issued claiming an improved formulation of cyclosporine in the form of a microemulsion pre-concentrate. In addition to the cyclosporine, this formulation requires a hydrophilic phase, a lipophilic phase, and a surfactant. The microemulsion pre-concentrate is claimed to provide enhanced bioavailability. The hydrophilic phase of the microemulsion concentrate comprises either 1,2-propylene glycol or:

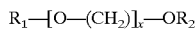

$$R_1-[O-(CH_2)]_x-OR_2$$

where $R_1$, $R_2=C_{1-5}$ alkyl or tetrahydrofurfuryl, and $x=1$ to 6. $R_2$ may also be hydrogen. Such ethers are commercially available under the trade name of Transcutol, Colycofurol and Glycofurol. The hydrophilic phase may additionally contain $C_{1-5}$ alkanols such as ethanol. The hydrophilic component of U.S. Pat. No. 5,342,625, an essential component for microemulsion preconcentrate, provides cosolvency for the cyclosporine.

The formulations of both U.S. Pat. Nos. 4,388,307 and 5,342,625 include the use of hydrophilic components, such as ethanol or 1,2-propylene glycol, which require specialized packaging, such as aluminum foil blister. U.S. Pat. No. 5,342,625 further requires the use of other ethers, such as Transcutol and Glycofurol, which are restricted by several regulatory agencies worldwide including the FDA because they are not considered "Generally Recognized As Safe" (GRAS) for oral use. Therefore, there is a need for an improved formulation that can be inexpensively and conventionally packaged, such as in glass or OHD polyethylene bottles. It is also desirable that the components of the formulation consist only of "GRAS" excipients for oral use.

The formulation of U.S. Pat. No. 5,154,930 requires a non-aqueous water-miscible solvent for the medication, preferably ethanol or a polyethylene glycol. The patent is different from the present invention not only in requiring the hydrophilic phase, but also in requiring a desalted charged lipid.

Alcohol-free emulsion pre-concentrates are known, but have drawbacks. For example, the formulation of U.S. Pat. No. 5,206,219 requires a multitude of ingredients, including the medication, a protease inhibitor, cholesterol, a phospholipid, a surfactant, a polyol and a lipid solvent. It is desirable to minimize the number of ingredients in order to reduce the chance of, for example, adverse reactions in the person taking the medication.

Kurihara, et al., U.S. Pat. No. 4,990,337, discloses improved solubility of cyclosporines in medium chain mono- and di-glycerides. All of the examples with cyclosporine and a surfactant involve making two solutions, one containing cyclosporine and a glyceride, and the other containing water and a surfactant. The two solutions are mixed and then emulsified with laboratory equipment.

We have discovered that if cyclosporine is dissolved in a polar lipid and mixed with a surfactant, then the mixture unexpectedly completely and reliably self-emulsifies upon contact with an aqueous phase such as water.

GENERAL DESCRIPTION OF THE INVENTION

The present invention is generally described as a "Polar Lipid Self-Emulsifying Drug Delivery System," (PLSEDDS) comprising a mixture of a medication dissolved in a polar lipid and mixed with sufficient surfactant, such that upon contact with an aqueous medium, the composition instantly and completely forms a fine emulsion of particle size from 0.1–14 microns. In the present invention, a novel pharmaceutical formulation for cyclosporine is provided in the form of a PLSEDDS which overcomes the problems associated with the use of hydrophilic cosolvents and a need for expensive specialized packaging and/or the non-"GRAS" hydrophilic component of U.S. Pat. No. 5,342,625. We have found that cyclosporine-A exhibits superior self-emulsification ability when dissolved in certain polar lipids, such as medium chain monoglyceride of $C_6$–$C_{12}$ fatty acids, having a monoglyceride content at of least 50%, and mixed with a sufficient amount of at least one surfactant. PLSEDDS compositions confer several desirable attributes to cyclosporine formulations. For example, PLSEDDS formulations described herein (i) provide instant fine emulsion on exposure to water or gastrointestinal fluid, (ii) utilize components having "GRAS" status, and (iii) do not need air tight aluminum blister packaging or other specialized expensive packaging.

It is one object of the present invention to provide a formulation for cyclosporine that upon contact with an aqueous medium, such as gastrointestinal fluid, instantly forms a fine emulsion.

It is another object of the present invention to provide an emulsion preconcentrate dosage formulation for hydrophobic drugs, other than cyclosporine, that are soluble in polar lipids. Such drugs include, but are not limited to, growth hormones, protease inhibitors, angiotensin-converting enzyme (ACE) inhibitors, cis- and trans-retinoids and their derivatives, parathyroids, insulins, as well as other water-insoluble peptides and proteins such as water-insoluble peptides having a molecular weight of about 400–3,000, and water-insoluble proteins having molecular weights above about 3,000.

It is another object of the present invention to provide a stable formulation for cyclosporine that does not require a hydrophilic phase. For example the present invention requires no ethanol, propylene glycol, or polyethylene glycol.

It is another object of the present invention to provide a formulation for cyclosporine that does not require non-"GRAS" components.

It is another object of the present invention to provide a formulation for cyclosporine that includes as major components only the medication, a polar lipid, and a surfactant. Here, a "major component" is one present in the formulation in an amount greater than about 1% by total weight.

It is another object of the present invention to provide a formulation for cyclosporine that does not require expensive specialized packaging.

DETAILED DESCRIPTION OF THE INVENTION

The cyclosporine composition of the present invention comprises a PLSEDDS and is composed of (i) cyclosporine or a mixture of cyclosporines as the active ingredient, (ii) a polar lipid component and (iii) a surfactant. An anti-oxidant may optionally be added. It was found that when cyclosporine is dissolved in certain polar lipids, such as medium chain monoglyceride of $C_6$–$C_{12}$ fatty acids, having a monoglyceride content of at least 50% (e.g., CAPMUL MCM), the presence of a sufficient amount of at least one surfactant in the cyclosporine solution obviated the need for the hydrophilic component of U.S. Pat. No. 5,342,625. The solubilization of cyclosporine in formulations containing CAPMUL MCM was found to be superior compared to any formulation containing hydrophilic and/or lipid materials without CAPMUL MCM. For example, formulation compositions without medium chain monoglyceride showed crystallization on storage at room temperature, thereby rendering them unsuitable for any practical use. The formulation of cyclosporine-A containing medium chain monoglyceride as a component prevented crystallization of cyclosporine under storage conditions.

The formulation composition containing medium chain monoglycerides as a vehicle for cyclosporine resulted in the following advantages: (i) elimination of the need for the hydrophilic component of U.S. Pat. No. 5,342,625; (ii) elimination of the need for specialized packaging such as blister packaging; (iii) utilization of "GRAS" materials for oral use and (iv) formation of a PLSEDDS suitable for oral administration.

The composition of the typical polar lipid self-emulsifying delivery system, PLSEDDS, comprises a mixture of cyclosporine, a polar lipid, such as a medium chain monoglyceride, and a surfactant. There is no need for a distinct hydrophilic phase. On exposure to an aqueous medium, such as water, the formulation of the present invention forms a fine emulsion with particle size in the range from about 0.1 to 14 microns.

The polar lipid is a medium chain monoglyceride of $C_6$–$C_{12}$ fatty acid with at least a 50% monoglyceride content. One source of such medium chain monoglycerides is marketed by Abitec Corp. under the trade name of CAPMUL MCM.

The surfactant may, for example, be polyglycolysed glycerides or ethoxylated glycerides having a molecular weight of PEG between 400 to 2,000 and a fatty acid chain length of between $C_6$–$C_{18}$. Sources of this, also known as PEG(8) caprylic-capric glyceride, include Labrasol, sold by Gattefosse of Leon, France, and Cremophor RH40, a PEG(40) castor oil sold by BASF Corporation of Midland, Mich. Other surfactants that may be used include polyoxyethylene sorbitan esters, i.e., lauryl, palmityl, stearyl, oleyl and trioleyl which are commercially available as Tween 20 (polysorbate 20), Tween 40 (polysorbate 40), Tween 60 (polysorbate 60), Tween 80 (polysorbate 80) and Tween 85 (polysorbate 85), respectively. These surfactants may be used singly or in combination. However, any surfactant, and any concentration of surfactant, can be utilized that enables self-emulsification of the composition when the composition is added to an aqueous solution.

A typical composition of the PLSEDDS comprises, by weight, about 5% to 20% cyclosporine, about 10% to 60% of a polar lipid, such as a medium chain monoglyceride, and about 30% to 70% of a surfactant or combination of surfactants. A more preferred composition comprises about 7.5% to 15% of cyclosporine, about 20% to 50% of polar lipid (medium chain monoglyceride) and about 40% to 60% surfactant. The most preferred composition comprises about 10% cyclosporine, about 40% polar lipid, and about 50% of surfactant.

The composition of the invention may further contain stabilizers such as antioxidants or preservatives. The formulation may be encapsulated, for example, in soft or hard gelatin capsules. Additionally, various known additives, such as sweetening agents, can be added.

PREFERRED EMBODIMENTS

The following examples provide data on some of the various compositions of the present invention. It should be understood that these examples are not meant to constitute a comprehensive list of the scope of the invention. Other formulations within the scope of the invention can be prepared, as will be understood by those of ordinary skill in the art. For example, the formulations herein described may be mixed with other ingredients to make a palatable liquid, and can include various ingredients such as flavoring agents, sweetening agents and diluents.

EXAMPLE 1

1.0 g of cyclosporine-A is dissolved in 5.0 g of CAPMUL MCM at 25° C. to 30° C. 6.0 g of Tween 80 are added and then mixed to achieve a homogeneous solution. The mixture appeared as a clear solution to the naked eye, and a microscopic analysis revealed no crystals. The formulation was filled in a soft gelatin capsule such that each capsule contained 50 mg of cyclosporine.

EXAMPLE 2

1.0 g of cyclosporine is dissolved in 2.3 g of CAPMUL (MCM) at 25° C. to 30° C. 4.5 g of Labrasol and 0.76 g of PEG-400 are added and mixed to achieve a homogenous solution. The mixture appeared as a clear solution to the naked eye, and a microscopic analysis revealed no crystals. The formulation was filled in a soft gelatin capsule such that each capsule contained 100 mg of cyclosporine.

EXAMPLES 3–5

The remaining examples are made according to the above procedure. The quantities are listed in the following table in grams:

| Ingredients | Example 3 | Example 4 | Example 5 |
|---|---|---|---|
| Cyclosporine | 0.50 | 0.50 | 0.50 |
| CAPMUL (MCM) | 2.50 | 2.00 | 2.00 |
| Labrasol | — | 1.26 | 1.26 |
| Tween 80 | 2.50 | 1.28 | 1.28* |
| Total | 5.50 | 5.04 | 5.04 |

*Tween 20

In each case, the mixture appeared as a clear solution to the naked eye, and a microscopic analysis revealed no crystals. The formulations were filled in soft gelatin capsules such that each capsule contained 50 mg of cyclosporine.

COMPARATIVE EXAMPLES 1–5

Five cyclosporine formulations were prepared without any medium chain monoglycerides according to the following table. All quantities are in grams.

| Ingredients | Example 1 | Example 2 | Example 3 | Example 4 | Example 5 |
|---|---|---|---|---|---|
| Cyclosporine | 1.00 | 0.50 | 1.00 | 1.00 | 0.50 |
| Labrasol | 5.04 | 2.50 | 2.50 | 9.01 | 2.52 |
| PEG-400 | 2.55 | 1.52 | 5.51 | 1.10 | — |
| Corn Oil | — | — | — | — | 2.51 |
| Total | 8.59 | 4.52 | 9.01 | 11.11 | 5.53 |

In each of the above cases the resulting mixture was a hazy liquid to the naked eye, and microscopic inspection revealed the presence of undissolved crystals.

We claim:

1. A pharmaceutical composition comprising:
   a) a cyclosporine or mixture of cyclosporines,
   b) a surfactant,
   c) a polar lipid comprising at least 50% medium chain monoglyceride of a fatty acid,
   which, on contact with an aqueous phase, forms a fine emulsion.

2. The composition of claim 1 where the cyclosporine is cyclosporine-A.

3. The composition of claim 1 where the polar lipid is a medium chain monoglyceride of $C_6$–$C_{12}$ fatty acids.

4. The composition of claim 1 where the fatty acid of the medium chain monoglyceride is caproic acid.

5. The composition of claim 1 where the polar lipid mixture comprises an amount greater than about 90% of medium chain monoglycerides of $C_6$–$C_{12}$ fatty acids.

6. The composition of claim 1 where the surfactant is polysorbate 80.

7. The composition of claim 1 where the surfactant is polysorbate 20.

8. The composition of claim 1 where the surfactant is a PEG(40) castor oil.

9. The composition of claim 1 where the surfactant comprises PEG(8) caprylic-capric glyceride and polysorbate 80.

10. The composition of claim 1 where the surfactant comprises PEG(8) caprylic-capric glyceride and PEG(40) castor oil.

11. The composition of claim 1 adapted for oral administration.

12. The composition of claim 1 in a solution dosage form for oral use.

13. The composition of claim 1 filled in a hard gelatin capsule.

14. The composition of claim 1 filled in a soft gelatin capsule.

15. The composition of claim 1 comprising about 5% to 20% cyclosporine based on the total weight of the composition.

16. The composition of claim 1 comprising about 7.5% to 15% cyclosporine based on the total weight of the composition.

17. The composition of claim 1 comprising about 10% cyclosporine based on the total weight of the composition.

18. The composition of claim 1 comprising about 10% to 60% polar lipid based on the total weight of the composition.

19. The composition of claim 1 comprising about 20% to 50% polar lipid based on the total weight of the composition.

20. The composition of claim 1 comprising about 40% polar lipid based on the total weight of the composition.

21. The composition of claim 1 comprising about 30% to 70% of surfactant or surfactants based on the total weight of the composition.

22. The composition of claim 1 comprising about 40% to 60% of surfactant or surfactants based on the total weight of the composition.

23. The composition of claim 1 comprising about 50% of surfactant or surfactants based on the total weight of the composition.

24. The composition of claim 1 which additionally contains about 0.2% antioxidant.

* * * * *